(12) United States Patent
Lemmens et al.

(10) Patent No.: US 7,339,056 B2
(45) Date of Patent: Mar. 4, 2008

(54) CONTINUOUS PROCESS FOR PREPARING CAPROLACTAM

(75) Inventors: Joannes Albertus Wilhelmus J. A. W. Lemmens, Roermond (NL); Frank F. Mostert, Maastricht (NL); Theodorus Maria T. M. Smeets, Elsloo (NL)

(73) Assignee: DSM IP Assets B.V., Heerlen (NL)

( * ) Notice: Subject to any disclaimer, the term of this patent is extended or adjusted under 35 U.S.C. 154(b) by 118 days.

(21) Appl. No.: 10/557,753

(22) PCT Filed: May 17, 2004

(86) PCT No.: PCT/EP2004/005643

§ 371 (c)(1),
(2), (4) Date: Nov. 21, 2005

(87) PCT Pub. No.: WO2004/103964

PCT Pub. Date: Dec. 2, 2004

(65) Prior Publication Data

US 2007/0055061 A1     Mar. 8, 2007

(30) Foreign Application Priority Data

May 23, 2003  (EP) .................. 03076589
May 23, 2003  (EP) .................. 03076590
May 23, 2003  (EP) .................. 03076591
May 23, 2003  (EP) .................. 03076592

(51) Int. Cl.
*C07D 201/04*    (2006.01)

(52) U.S. Cl. .................................. 540/535

(58) Field of Classification Search ................ 540/535
See application file for complete search history.

(56) References Cited

U.S. PATENT DOCUMENTS

| 2,237,365 | A | 4/1941 | Schlack et al. |
| 3,914,217 | A | 10/1975 | Smith |
| 3,953,438 | A | 4/1976 | Koppel |

FOREIGN PATENT DOCUMENTS

EP     0 785 188     7/1997

OTHER PUBLICATIONS

U.S. Appl. No. 10/557,771, filed Nov. 29, 2006.

*Primary Examiner*—Bruck Kifle
(74) *Attorney, Agent, or Firm*—Nixon & Vanderhye P.C.

(57) ABSTRACT

The invention relates to a continuous process for preparing caprolactam by Beckmann rearrangement of cyclohexanone oxime, said process comprising
  a) feeding (i) oleum and (ii) cyclohexanone oxime into a first reaction mixture comprising caprolactam, sulfuric acid and $SO_3$,
  b) feeding (iii) a portion of the first reaction mixture and (iv) cyclohexanone oxime into a second reaction mixture comprising caprolactam, sulfuric acid and $SO_3$,
  c) withdrawing a portion of the second reaction mixture, wherein the process further comprises obtaining the cyclohexanone oxime that is fed to the reaction mixtures by:
    1) preparing an organic medium comprising cyclohexanone oxime dissolved in an organic solvent
    2) separating, by distillation, cyclohexanone oxime from said organic medium.

18 Claims, 3 Drawing Sheets

CONTINUOUS PROCESS FOR PREPARING CAPROLACTAM

This application is the U.S. national phase of international application PCT/EP2004/005643 filed 17 May 2004 which designated the U.S. and claims benefit of EP 03076590.3, EP 03076591.1, EP 03076589.5 and EP 03076592.9, dated 23 May 2003, respectively, the entire content of which is hereby incorporated by reference.

FIELD OF INVENTION

The invention relates to a continuous process for preparing caprolactam by Beckmann rearrangement of cyclohexanone oxime, said process comprising
a) feeding (i) oleum and (ii) cyclohexanone oxime into a first reaction mixture comprising caprolactam, sulfuric acid and $SO_3$,
b) feeding (iii) a portion of the first reaction mixture and (iv) cyclohexanone oxime into a second reaction mixture comprising caprolactam, sulfuric acid and $SO_3$,
c) withdrawing a portion of the second reaction mixture.

BACKGROUND AND SUMMARY OF INVENTION

Caprolactam can be prepared by Beckmann rearrangement of cyclohexanone oxime. Such Beckmann rearrangement can be carried out by admixing cyclohexanone oxime to a reaction mixture comprising caprolactam, sulfuric acid and $SO_3$. In such process the sulfuric acid and $SO_3$ is a catalyst for the conversion of cyclohexanone oxime towards caprolactam. Such conversion is known to occur instantaneously.

Such a process is described in U.S. Pat. No. 3,953,438. In this process cyclohexanone oxime containing 4.9 wt. % water and oleum containing 25 weight percent $SO_3$ are continuously fed to a first rearrangement zone containing a circulating reaction mass such that the circulating reaction mass having a sulfuric acid +$SO_3$ to caprolactam weight ratio of 1.45 and a $SO_3$ content of 5.9 weight percent. A portion of the reaction mass of the first catalytic rearrangement zone equivalent to the feed thereto is continuously removed and fed to a second rearrangement zone containing a circulating reaction mass. Cyclohexanone oxime containing 4.9 wt. % water is also continuously fed to the circulating reaction mass of the second rearrangement zone. The circulating reaction mass of the second rearrangement zone has a sulfuric acid +$SO_3$ to caprolactam weight ratio of 1.14 and a $SO_3$ content of 3.2 weight percent. A portion of the reaction mass of the second catalytic rearrangement zone equivalent to the feed thereto is withdrawn.

In U.S. Pat. No. 3,953,438 it is described that the oxime may contain up to 6 wt. % water. Although a value of 0.1 wt. % water is mentioned as a lower limit, in fact, the process disclosed in this patent is carried out at high water content, i.e. in all the examples oxime containing 4.9 wt. % of water is used. No method is given how to reduce the water content of the oxime.

In the process of U.S. Pat. No. 3,953,438 oleum having relatively high oleum strength is needed. Hence large quantities of $SO_3$ are needed to obtain the desired yield to caprolactam.

The object of the invention is to improve the yield while using relatively small amounts of $SO_3$.

This object is achieved in that the process further comprises obtaining the cyclohexanone oxime that is fed to the reaction mixtures by:
1) preparing an organic medium comprising cyclohexanone oxime dissolved in an organic solvent;
2) separating, by distillation, cyclohexanone oxime from said organic medium

DETAILED DESCRIPTION OF THE INVENTION

It has been found that with the process of the present invention less $SO_3$ needs to be added for obtaining a high yield to caprolactam. Adding high quantities of $SO_3$ is disadvantageous, since, either a high $SO_3$ concentration in the oleum ($H_2SO_4$/$SO_3$ mixture) has to be applied, which is disadvantageous from an economical point of view and because the risk of fuming of the oleum increases and because the flowability of the oleum decreases or, when still using a relatively low concentration of $SO_3$ in the oleum, high quantities of oleum has to be fed to the rearrangement mixture per quantity of oxime, which results in the formation of high amounts of by-product (ammonium sulfate) during subsequent neutralization.

In the process of the present invention either a higher yield to caprolactam can be obtained for a given amount of $SO_3$ added to the process, or less $SO_3$ needs to be added to obtain a given yield to caprolactam. In addition, with the process of the invention either an improved quality of the obtained caprolactam can be obtained for a given amount of $SO_3$ added to the process, or less $SO_3$ needs to be added to obtain a given quality to caprolactam.

The cyclohexanone oxime fed to the reaction mixtures is obtained by:
1) preparing an organic medium comprising cyclohexanone oxime dissolved in an organic solvent
2) separating, by distillation, cyclohexanone oxime from said organic medium.

Preparing an organic medium comprising cyclohexanone oxime dissolved in an organic solvent is preferably carried out by contacting in a reaction zone (herein after referred to as cyclohexanone oxime synthesis zone) in countercurrent flow a stream of a solution of cyclohexanone in an organic solvent which is also a solvent for the cyclohexanone oxime and a stream of a phosphate buffered, aqueous solution of hydroxylammonium; and withdrawing from the reaction zone an organic medium of cyclohexanone oxime dissolved in said organic solvent. Particularly suitable organic solvent for use in the process for preparing cyclohexanone oxime are toluene and benzene. Preferably toluene is used as organic solvent. The phosphate buffered, aqueous reaction medium is preferably continuously recycled between a hydroxylammonium synthesis zone and a cyclohexanone oxime synthesis zone. In the hydroxylammonium synthesis zone hydroxylammonium is formed by catalytic reduction of nitrate ions or nitric oxide with hydrogen. In the cyclohexanone oxime synthesis zone, hydroxylammonium formed in the hydroxylammonium synthesis zone reacts with cyclohexanone to form cyclohexanone oxime. The cyclohexanone oxime can then be separated from the aqueous reaction medium which is recycled to the hydroxylammonium synthesis zone. An organic medium comprising the formed cyclohexanone oxime dissolved in said organic solvent is withdrawn from the reaction zone, and distilled to recover cyclohexanone oxime having a water content less than 2 wt. %, preferably less than 1 wt. %, more preferably even less than 0.2 wt. % and even more preferably less than 0.1 wt. %. Said recovered cyclohexanone oxime is fed to the reaction mixtures in the process according to the invention.

The organic medium generally comprises cyclohexanone oxime, said organic solvent and optionally cyclohexanone. In case the organic medium comprises cyclohexanone, the concentration of cyclohexanone in the organic medium may be higher than 0.1 wt. %, preferably higher than 0.5 wt. %, most preferably higher than 1 wt. %. The concentration of cyclohexanone in the organic medium may be lower than 10 wt. %, preferably lower than 5 wt. %. The concentration of cyclohexanone oxime in the organic medium may be higher than 5 wt. %, preferably higher than 10 wt. %, more preferably higher than 25 wt. %, and may be lower than 60 wt. %, preferably lower than 50 wt. %. The concentration of organic solvent in the organic medium may be higher than 40 wt. %, preferably higher than 50 wt. %, and may be lower than 95 wt. %, preferably lower than 90 wt. %.

In the process of the invention, separating cyclohexanone oxime from said organic medium is effected by distillation. The distillation can be effected in any suitable manner. The distillation may be carried out using any suitable column or combination of columns. In one embodiment, the separation by distillation comprises distilling the organic medium to obtain organic solvent as a distillate (overhead product) and cyclohexanone oxime as a bottom product. The cyclohexanone oxime, e.g. obtained as a bottom product may for instance comprise less than 2 wt. %, preferably less than 1 wt. %, more preferably less than 0.2 wt. %, more preferably less than 0.1 wt. % of water, and may be fed to the first reaction mixture, the second reaction mixture and, optionally the third reaction mixture. The distillation may be carried out at any suitable temperature, for instance between 35 and 115° C., preferably between 50 and 100° C., and at any suitable pressure, for instance between 0.006 and 0.020 MPa, preferably between 0.012 and 0.020 MPa. As used herein, the temperature refers to the temperature in the top of a column in which the distillation is effected. As used herein, the pressure refers to the pressure in the top of a column in which the distillation is effected. Examples for effecting the distillation are described in GB-A-1303739 and EP-A-5291.

In a preferred embodiment, the process comprises a) feeding (I) oleum and (ii) cyclohexanone oxime into a first reaction mixture comprising caprolactam, sulfuric acid and SO$_3$; b) feeding (iii) a portion of the first reaction mixture and (iv) cyclohexanone oxime into a second reaction mixture comprising caprolactam, sulfuric acid and SO$_3$; c) withdrawing a portion of the second reaction mixture; d) feeding (v) a portion of the second reaction mixture and (vi) cyclohexanone oxime into a third reaction mixture comprising caprolactam, sulfuric acid and SO$_3$; e) withdrawing a portion of the third reaction mixture; and wherein the process further comprises obtaining the cyclohexanone oxime introduced into the reaction mixtures by:

1) preparing an organic medium comprising cyclohexanone oxime dissolved in an organic solvent;
2) separating, by distillation, cyclohexanone oxime from said organic medium.

Preferably, the first reaction mixture, the second reaction mixture and, if applicable, the third reaction mixture are kept in circulation.

In such more stage rearrangement, the Beckmann rearrangement in each stage is preferably carried out in a circulating reaction mixture comprising caprolactam, sulfuric acid and SO$_3$ by continuously feeding cyclohexanone oxime and, separately therefrom, oleum (first stage) resp. the amount of the circulating reaction mixture withdrawn from the previous stage (if any) to the circulating reaction mixture and by continuously withdrawing an amount of the circulating reaction mixture equivalent to the amount of cyclohexanone oxime and the amount of oleum (first stage) resp. the amount of the circulating reaction mixture withdrawn from the previous stage (if any) introduced to the circulating reaction mixture and by continuously feeding said amount to the next stage (if any). In the last stage of a more stage rearrangement a portion of the circulating reaction mixture is withdrawn equivalent to the amount of cyclohexanone oxime and the amount of the circulating reaction mixture withdrawn from the previous stage introduced into the circulating reaction mixture of the last stage; from said portion caprolactam is recovered.

The first reaction mixture, the second reaction mixture, and the optional third reaction mixture comprise caprolactam, sulfuric acid and SO$_3$. The molar ratio M of the reaction mixture is defined as $(n_{SO3}+n_{H2SO4})/n_{cap}$, wherein $n_{SO3}$=quantity of SO$_3$ in reaction mixture, in mol (1 mol SO$_3$ corresponds to 80 g), $n_{H2SO4}$=quantity of H$_2$SO$_4$ in reaction mixture, in mol (1 mol H$_2$SO$_4$ corresponds to 98 g) and $n_{cap}$=quantity of caprolactam in reaction mixture, in mol (1 mol caprolactam corresponds to 113 g). With SO$_3$ content (wt. %) is meant the amount of SO$_3$ (g) relative to the total amount (g) of reaction mixture comprising sulfuric acid, SO$_3$ and caprolactam.

In one preferred embodiment of the invention, the rearrangement is carried out in two stages connected in series. In this embodiment, caprolactam is preferably obtained by a continuous process comprising a) feeding (i) oleum and (ii) cyclohexanone oxime into a first reaction mixture comprising caprolactam, sulfuric acid and SO$_3$,
b) feeding (iii) a portion of the first reaction mixture and (iv) cyclohexanone oxime into a second reaction mixture comprising caprolactam, sulfuric acid and SO$_3$, wherein the molar ratio M of the second reaction mixture is between 1.0 and 1.4 and the SO$_3$ content of the second reaction mixture is higher than 6 wt. %, more preferably higher than 8 wt. % and even more preferably higher than 10 wt. % and the SO$_3$ content of the second reaction mixture is preferably lower than 20 wt. %, more preferably lower than 18 wt. % and even more preferably lower than 16 wt. %,
c) withdrawing a portion of the second reaction mixture from which caprolactam is recovered, and wherein the process further comprises obtaining the cyclohexanone oxime introduced into the reaction mixtures by:
1) preparing an organic medium comprising cyclohexanone oxime dissolved in an organic solvent;
2) separating, by distillation, cyclohexanone oxime from said organic medium. Preferably, the first reaction mixture and the second reaction mixture are kept in circulation.

In an even more preferred embodiment of the invention, the rearrangement is carried out in three stages connected in series. In this embodiment, caprolactam is obtained by a continuous process comprising a) feeding (i) oleum and (ii) cyclohexanone oxime into a first reaction mixture comprising caprolactam, sulfuric acid and $SO_3$,
b) feeding (iii) a portion of the first reaction mixture and (iv) cyclohexanone oxime into a second reaction mixture comprising caprolactam, sulfuric acid and $SO_3$,
c) withdrawing a portion of the second reaction mixture,
d) feeding (v) a portion of the second reaction mixture and (vi) cyclohexanone oxime into a third reaction mixture comprising caprolactam, sulfuric acid and $SO_3$, wherein the molar ratio M of the third reaction mixture is between 1.0 and 1.4 and the $SO_3$ content of the third reaction mixture is higher than 6 wt. %, more preferably higher than 8 wt. % and even more preferably higher than 10 wt. % and the $SO_3$ content of the third reaction mixture is preferably lower than 18 wt. %, more preferably lower than 17 wt. % and even more preferably lower than 16 wt. %,
e) withdrawing a portion of the third reaction mixture from which caprolactam is recovered and wherein the process further comprises obtaining the cyclohexanone oxime introduced into the reaction mixtures by:
1) preparing an organic medium comprising cyclohexanone oxime dissolved in an organic solvent;
2) separating, by distillation, cyclohexanone oxime from said organic medium.

Preferably, the first reaction mixture, the second reaction mixture and the third reaction mixture are kept in circulation.

Working at such low molar ratio and high $SO_3$ content in especially the last stage of a more stage rearrangement is advantageous as low molar ratios in the last stage of a more stage rearrangement results in the formation of small amounts of ammonium sulfate during subsequent neutralisation while high amounts of $SO_3$ at such low molar ratio results in an improved yield to caprolactam and additionally results in an improved quality of the obtained caprolactam.

The molar ratio M is preferably different in each reaction mixture. The molar ratio M in the first, second and, if applicable, third reaction mixture will, as used herein, be referred to as M(1), M(2) and M(3) respectively. The concentration $SO_3$ in the first, second, and, if applicable, third reaction mixture will, as used herein, be referred to as $C_{SO3}(1)$, $C_{SO3}(2)$ and $C_{SO3}(3)$. The temperature in the first, second and, if applicable, third reaction mixture will, as used herein, be referred to as T(1), T(2) and T(3) respectively. As used herein, the values for M, the $SO_3$ concentration, and the temperature refer in particular to the value in the reaction mixture obtained after feeding of the cyclohexanone oxime into the reaction mixture.

The $SO_3$ content of the reaction mixtures comprising caprolactam, sulfuric acid and $SO_3$ is preferably higher than 6 wt. %, more preferably higher than 8 wt. % and even more preferably higher than 10 wt. %. For practical reasons the $SO_3$ content of the reaction mixtures is usually less than 20 wt. %, for instance less than 18 wt. %, for instance less than 17 wt. %. The molar ratio M of the reaction mixtures is preferably between 1 and 2.2, more preferably between 1.1 and 1.9.

The temperature at which the Beckmann rearrangement is carried out is preferably between 70 and 130° C., more preferably at a temperature of between 70 and 120° C.

Preferred values for M and the $SO_3$ concentration can be obtained by feeding cyclohexanone oxime to the different stages in appropriate amounts, and by applying appropriate quantities of oleum of appropriate $SO_3$ concentration.

Preferably, M(2) is lower than M(1). Preferably M(3) is lower than M(2).

In a preferred embodiment, M(1) is between 1.2 and 2.2, preferably between 1.4 and 1.9, more preferably between 1.5 and 1.8. Preferably, $C_{SO3}(1)$ is between 3 and 20 wt. %, preferably higher than 5 wt. % and more preferably higher than 6 wt. %. Increased values for $C_{SO3}(1)$ have the advantage that $C_{SO3}(2)$ can be kept high in the second reaction mixture without having to feed oleum to the second reaction mixture. $C_{SO3}(1)$ is preferably less than 18 wt. % and even more preferably less than 17 wt. %. Preferably T(1) is between 70 and 130° C., more preferably between 70 and 120° C.

In a preferred embodiment M(2) is between 1.0 and 1.6, preferably between 1.2 and 1.5. Preferably, $C_{SO3}(2)$ is between 2 and 20 wt. %, more preferably higher than 6 wt. %, more preferably higher than 8 wt. %. Increased concentrations of $C_{SO3}(2)$ within the abovementioned ranges for M(2) were surprisingly found to result in significantly higher yields. $C_{SO3}(2)$ is preferably less than 17 wt. % and even more preferably less than 16 wt. %. Preferably T(2) is between 70 and 130° C. and more preferably between 80 and 120° C.

In a preferred embodiment M(3) is between 1.0 and 1.4 and preferably between 1.0 and 1.3. Preferably, $C_{SO3}(3)$ is between 4 and 18 wt. %, preferably higher than 6 wt. %, more preferably higher than 8 wt. %. Increased concentrations of $C_{SO3}(3)$ within the abovementioned ranges for M(3) were surprisingly found to result in significantly higher yields. $C_{SO3}(3)$ is preferably less than 17 wt. % and even more preferably less than 16 wt. %. Preferably T(3) is between 80 and 130° C. and more preferably between 80 and 120° C.

The values for M and the $SO_3$ content may be obtained in any suitable way. In a preferred embodiment, the process is a continuous process comprising keeping the reaction mixture in circulation, feeding a mixture comprising sulfuric acid and $SO_3$, for instance oleum or a reaction mixture comprising caprolactam, sulfuric acid and $SO_3$ to the circulating reaction mixture, and withdrawing part of the circulating reaction mixture. The amount of mixture comprising sulfuric acid and $SO_3$, the $SO_3$ content thereof and the amount of cyclohexanone oxime fed to the circulating reaction mixture may be chosen such that M and the $SO_3$ content of the reaction mixture have the preferred values. Oleum may have any suitable $SO_3$ concentration, for instance 18 to 35 wt. % $SO_3$.

In the process of the invention, the rearrangement is carried out in a plurality of stages connected in series in which the molar ratio M of the reaction mixture preferably decreases in each further stage. Preferably, the rearrangement is carried out in at least two stages and more preferably in at least three stages connected in series. Oleum may be fed into the reaction mixture in any suitable way. Preferably all oleum applied is fed into the first reaction mixture, while preferably cyclohexanone oxime is fed to the first, second, and, if applicable, to the third reaction mixture. Preferably, the amount of cyclohexanone oxime fed to the first reaction mixture is larger than the amount of cyclohexanone oxime fed to the second reaction mixture, and, if applicable, preferably the amount of cyclohexanone oxime fed to the second reaction mixture is larger than the amount of cyclohexanone oxime fed to the third reaction mixture. This is advantageous as, due to the lower molar ratio in each further stage, the yield to caprolactam decreases in each further stage. Feeding cyclohexanone oxime to each stage with an amount decreasing from each stage results in that the overall high yield to caprolactam is maintained with a comparable lower ammonium sulfate by-product formation. Preferably, from 60 to 95 wt. % of the total amount of cyclohexanone oxime fed into the first, second and, if applicable, third reaction mixture, is fed into the first reaction mixture. Preferably, from 5 to 40 wt. % of the total amount of cyclohexanone oxime fed into the first, second and, if applicable, third reaction mixture is fed into the second reaction mixture. If applicable, preferably, from 2 to 15 wt. % of the total amount of cyclohexanone oxime fed into the first, second and third reaction mixture is fed into the third reaction mixture.

Preferably, one parts by volume of cyclohexanone oxime is continuously introduced into at least 10 parts by volume, more preferably at least 20 parts by volume of reaction mixture.

Cyclohexanone oxime is preferably fed to the reaction mixture in the form of a liquid melt.

Figure 2:
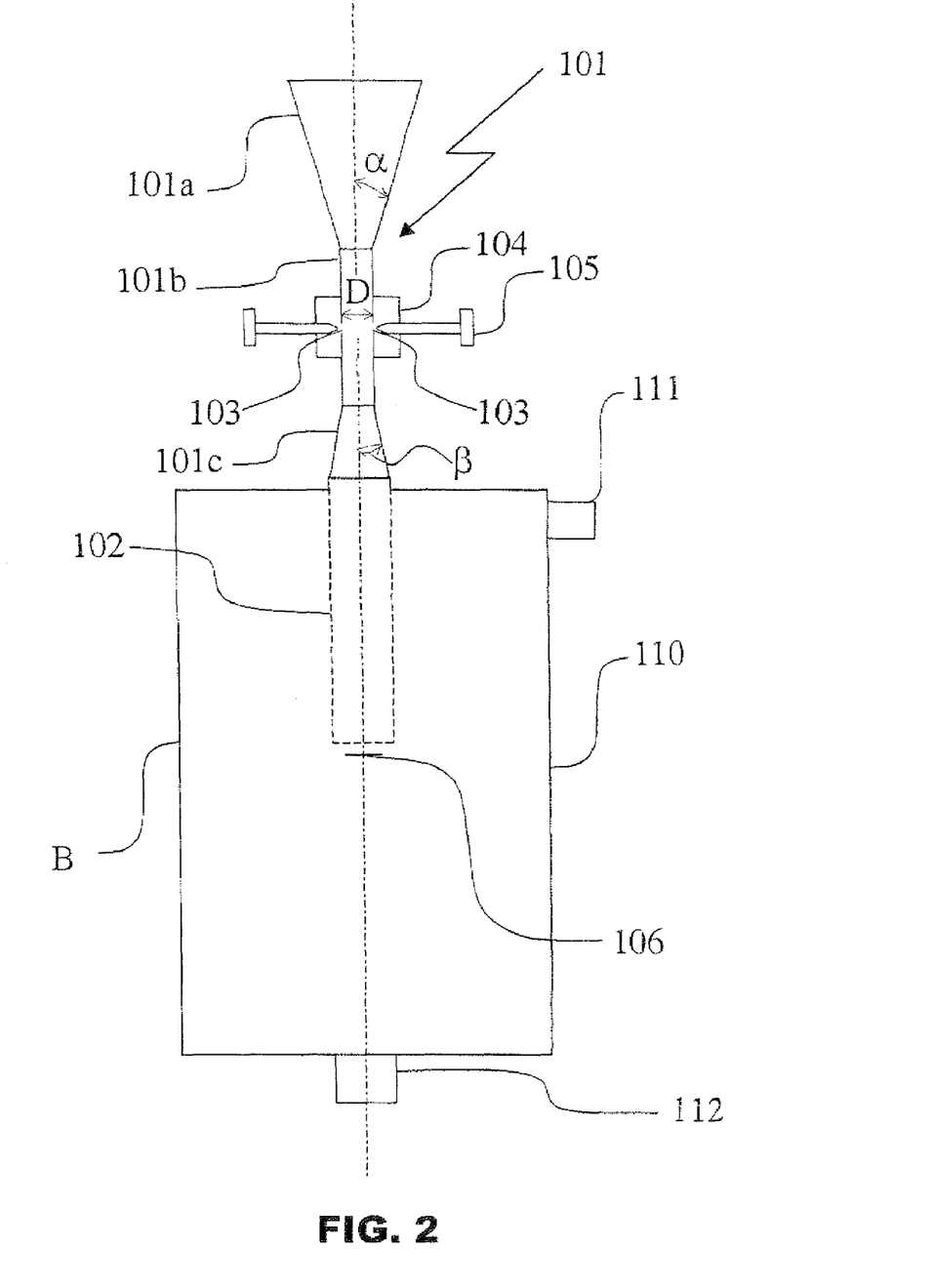
FIG. 2 is a schematic view of a mixing device that is preferably used as the mixing devices A1, A2 and A3 depicted in FIG. 1.

Cyclohexanone oxime and, separately therefrom, oleum are preferably introduced via dividers. Preferably cyclohexanone oxime is intensively mixed with the reaction mixture. Suitable methods for admixture of cyclohexanone oxime with the reaction mixture are for example described in U.S. Pat. No. 3,601,318 and EP-A-15617. In a preferred embodiment of the invention, cyclohexanone oxime is admixed to the reaction mixture using a mixing device as depicted in FIG. 2. In FIG. 2, the mixing device comprises a cylindrical tube 101 that in first part 101a narrows to throat 101b, and beyond throat 101b widens in a second part 101c. The second part 101c of the tube is connected to a second tube 102. In the throat openings 103 are present which are in connection with feed chamber 104. Cyclohexanone oxime is supplied via feed chamber 104, and fed into reaction mixture through openings 103. The mixing device comprises closures 105 with which openings 103 can be opened and closed independently. The mixing device also comprises a baffle 106 opposite to the exit of tube 101. The tube opens into collecting vessel B, having walls 110, overflow 111, and outlet 112. Reaction mixture leaving tube 102 is collected in the collecting vessel B, and leaves collecting vessel B partly via line 112 to be further circulated, and partly via overflow 111 to be fed into a subsequent reaction mixture or for the recovery of caprolactam. In a more preferred embodiment of the invention, the mixing device comprises (i) a tube through which the reaction mixture can flow, and (ii) channels disposed around the tube, said channels opening into the tube, said process comprising: passing the reaction mixture through the tube, and feeding the cyclohexanone oxime into the reaction mixture through one or more of said channels, wherein Re of the reaction mixture >5000, preferably higher than 10.000, Re being the Reynolds number as defined by $\rho \cdot V \cdot D/\eta$, wherein $\rho$=density (in kg/m$^3$) of the reaction mixture that is fed to the tube V=velocity of the reaction mixture, V being defined as W/A, wherein W is the flow rate (in m$^3$/s) of the reaction mixture that is fed into the tube and A is the cross section area of the tube (in m$^2$) at the level where said channels open into the tube.

D=diameter of the tube at the level where said channels open into the tube (in m).

$\eta$=viscosity of the reaction mixture that is fed into the tube (in Pa·s).

The recovery of caprolactam from the reaction mixture obtained in the last stage of the Beckmann rearrangement may be performed by known methods. Preferably, the reaction mixture obtained in the last stage of the Beckmann rearrangement is neutralized with ammonia in water and the ammonium sulfate thus formed is removed from the caprolactam solution. The caprolactam solution may be purified by known procedures.

DESCRIPTION OF PREFERRED EMBODIMENT

Figure 1:
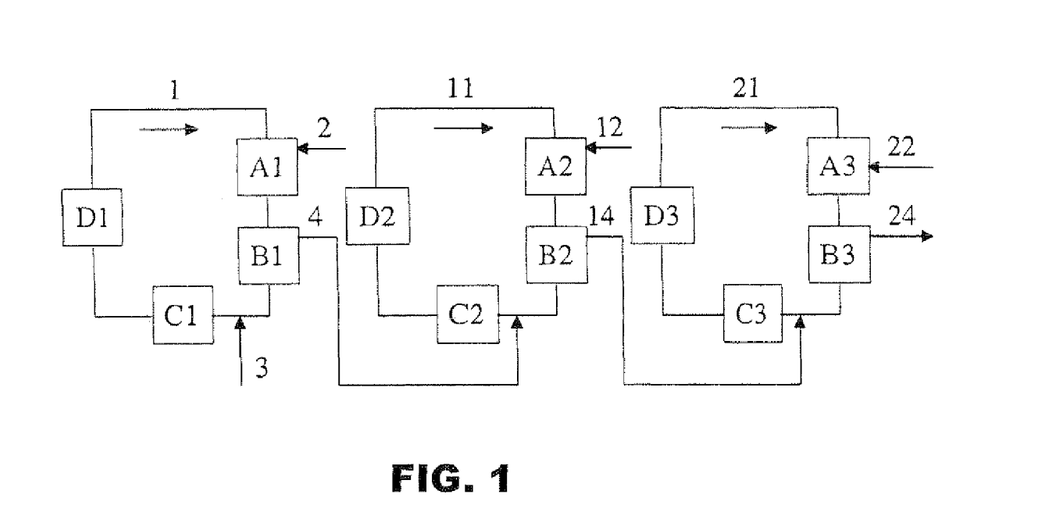
FIG. 1 is a schematic diagram of a three-stage Beckman rearrangement process for preparing caprolactam according to an embodiment of the invention.

FIG. 1 shows a preferred set-up for a rearrangement in three stages comprising a first circulation system, a second circulation system and a third circulation system. The first circulation system comprises mixing device A1, collecting vessel B1, pump C1 and cooler D1, and a first reaction mixture is kept in circulation via line 1. The second circulation system comprises mixing device A2, collecting vessel B2, pump C2 and cooler D2, and a second reaction mixture is kept in circulation via line 11. The third circulation system comprises mixing device A3, collecting vessel B3, pump C3 and cooler D3, and a third reaction mixture is kept in circulation via line 21. Cyclohexanone oxime and oleum are fed into the first reaction mixture via line 2 and line 3 respectively. A portion of the first reaction mixture is withdrawn from collecting vessel B1 via line 4 and fed into the second reaction mixture. Cyclohexanone oxime is fed into the second reaction mixture via line 12. A portion of the second reaction mixture is withdrawn from collecting vessel B2 via line 14 and fed into the third reaction mixture. Cyclohexanone oxime is fed to the third reaction mixture via line 22. A portion of the third reaction mixture is withdrawn from collecting vessel B3 via line 24. The process is carried out continuously.

FIG. 2 shows a mixing device that is preferably used as mixing device A1, mixing device A2, and mixing device A3.

The following specific examples are to be construed as merely illustrative, and not limitative, of the remainder of the disclosure. In the examples the yield to caprolactam was determined as follows: Samples were taken from the reaction mixture leaving the last stage of the rearrangement. The yield (amount of caprolactam formed per amount of cyclohexanone oxime fed to the reaction mixture(s) was determined as follows: To a first part (0.2 g) of each sample concentrated sulfuric acid (20 ml, 96wt %) was added, as well as 15 g K$_2$SO$_4$ and 0.7 g HgO. The nitrogen content of the resulting acidic mixture was determined using the Kjeldahl Method, from which the molar concentration of nitrogen in the first part of the sample (TN) was calculated. A second part of each sample is extracted with chloroform. This method is based on the fact that caprolactam enters the chloroform phase. The impurities stay in the water phase. The extracted aqueous phase is analyzed for its nitrogen content by the Kjeldahl Method, from which the molar concentration of nitrogen in the second part of the sample (RN) was calculated. The yield is calculated as follows:

$$\% \text{ yield} = \left(1 - \frac{RN}{TN}\right) \times 100$$

The absorbance at 290 nm (E$_{290}$), used as quality specification of the obtained caprolatam, was determined as follows:

The reaction mixture leaving the last stage of the rearrangement was neutralized with ammonia, and the resulting caprolactam-containing aqueous phase was separated. The absorbance of the separated caprolactam-containing aqueous phase was measured at a wavelength of 290 nm using a 1 cm cuvette (calculated for a 70 wt. % aqueous caprolactam solution).

EXAMPLE 1

This is an example of the preparation of cyclohexanone oxime by reaction of a buffered hydroxylammonium phosphate solution and cyclohexanone in the presence of toluene.

Figure 3:
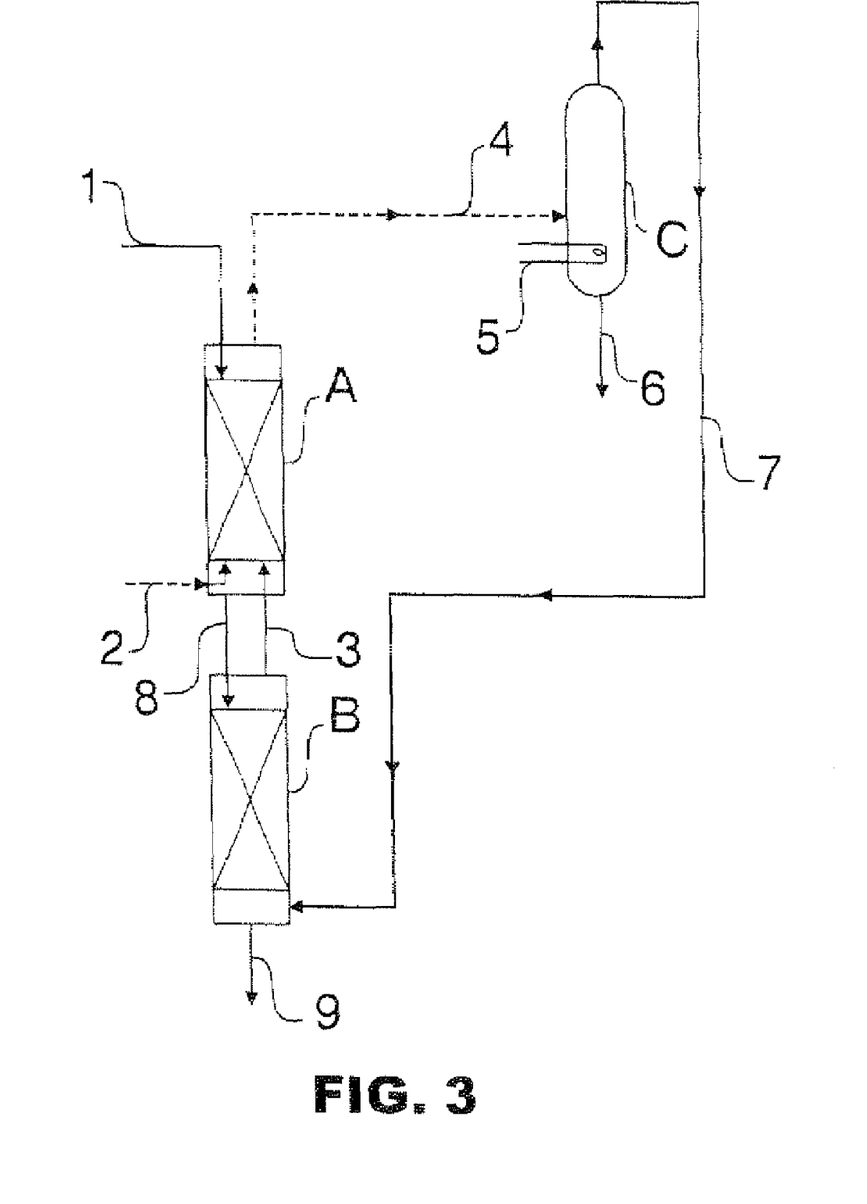
FIG. 3 is a schematic view of a process for preparing employed in Example 1 below.

Using the process according to FIG. 3, the following hydroxylammonium salt solution was fed to counter-current reactor A via line 1, per unit time:
65 kmoles of $NH_2OH.H_3PO_4$
97 kmoles of $NH_4H_2PO_4$
38 kmoles of $H_3PO_4$
191 kmoles of $NH_4NO_3$ and
3184 kmoles of $H_2O$.

The said solution was derived from a hydroxylamine synthesis stage in which nitrate ions, supplied in the form of 55% by weight of nitric acid, were reduced to hydroxylamine with the aid of hydrogen in a medium buffered with the aid of a combination of phosphate and phosphoric acid and in the presence of a platinum catalyst. The pH of the solution was 2.1.

A further solution of 65 kmoles of cyclohexanone, and a toluene stream containing:
400 kmoles of toluene,
9 kmoles of cyclohexanone,
2 kmoles of oxime and
5 kmoles of $H_2O$, were admitted to the said reactor A via the lines 2 and 3, respectively.

The temperature in the reactor A was maintained at 70° C.

An oxime-containing toluene product stream was discharged from the reactor through line 4 to distillation column C provided with a heating spiral 5. The said product stream contained:
400 kmoles of toluene,
65 kmoles of oxime and
20 kmoles of $H_2O$.

In column C, separation into oxime and toluene was effected. 65 kmoles of oxime per unit time were discharged via line 6, while toluene (400 kmoles) and water (20 kmoles) were discharged to extraction column B via line 7.

An aqueous solution was discharged per unit time via line 8 to extraction column B containing:
191 kmoles of $NH_4NO_3$
97 kmoles of $NH_4H_2PO_4$
103 kmoles of $H_3PO_4$
9 kmoles of cyclohexanone,
2 kmoles of oxime and
3234 kmoles of $H_2O$.

After removal of toluene dissolved therein by stripping, the aqueous solution discharged from extraction column B had the following composition:
97 kmoles of $NH_4H_2PO_4$
191 kmoles of $HN_4NO_3$
103 kmoles of $H_3PO_4$ and
3249 kmoles of $H_2O$.

This solution was recycled to the hydroxylamine synthesis stage to serve as the reaction medium in the reduction of nitric acid to hydroxylamine.

The oxime obtained in column C contains less than 1000 ppm water. Said oxime was used in Examples 2-4 given below.

Comparitive Experiment A

A set-up was used as depicted in FIGS. 1 and 2. To the first stage of a rearrangement system 7.1 t/hr oxim containing 4.7% water is fed (2) and 9.2 t/hr oleum containing 25 wt. % $SO_3$ (3). The temperature in the pump vessel (C1) is maintained at 102° C. by circulating the first reaction mixture at a rate of 400 t/hr over a cooler (D1) in which its temperature is lowered to 77° C. The oxime is mixed into the circulating first reaction mixture through a mixing device (A1) having a throat diameter of 51 mm (101b) and the mixing device was provided with 16 channels (diameter 3 mm). Cyclohexanone oxime was fed through 8 channels (8 of the channels being in closed position). The velocity of the circulating mixture in the throat is 40 m/s and the velocity at which cyclohexanone oxime is fed to the circulating reaction mixture is 41 m/s. The reactor discharge (4) is sent to the second stage of the rearrangement system where 1.9 t/hr oxime of identical origine is added (12). In the second and third stage of the rearrangement system the oxime is mixed into the circulating second and third reaction mixture respectively through a mixing device (A2 and A3 respectively) as used in the first stage but of which the dimensions are adapted to the lower throughput in the second and third stage. Circulation rate is 150 t/hr and cooler (D2) outlet temperature is 72° C. and the reactor operates at 86° C. Finally the reactor discharge (14) is sent to the third stage of the rearrangement system where 1.1 t/hr oxime is added (22). Operating temperature is again 86° C. controlled by circulating rate of 100 t/hr and cooler (D3) outlet temperature of 76° C.

The molar ratios of the first, second resp. third reaction mixture are 1.68, 1.32 and 1.18 respectively, which corresponds to weight ratios of 1.46, 1.15 and 1.02 resp. The weight ratio of the reaction mixture is defined as (quantity of $SO_3$ in reaction mixture+quantity of $H_2SO_4$ in reaction mixture)/quantity of caprolactam in reaction mixture. The $SO_3$ concentration of the first, second resp. third reaction mixture were: 4.8%, 2.1% and 0.8% resp. The overall yield of the 3-stage rearrangement system was determined using the above given method: 98.9%. The extinction at 290 nm (determined as given above) was 3.54.

EXAMPLE 2

Comparitive Experiment was repeated with the difference that cyclohexanone oxime as prepared according to example 1 was used. The oxime feed rates to the three rearrangement stages were almost identical as in Comparative Experiment A. The oleum feed rate was not adjusted resulting in lower oleum to oxime consumption ratios compared with Comparative Experiment A.

Circulation rates were maintained as in Comparative Experiment A and cooling temperatures were slightly adjusted in order to be able to keep the reactor temperatures on a same level as in Comparative Experiment A.

The molar ratios of the first, second resp. third reaction mixture are 1.58, 1.24 and 1.11 resp. The $SO_3$ concentration of the first, second and third reaction mixture resp. were 14.2%, 12.7% and 12.0% resp. and the overall yield measured in the discharge of the $3^{rd}$ reactor was determined with the above given method to be 99.4%. The extinction at 290 nm (determined as given above) was 0.65.

EXAMPLE 3

Comparative Experiment A was repeated with the difference that cyclohexanone oxime as prepared according to example 1 was used and that, to ensure similar oleum to oxime consumption ratios, the oleum feed was reduced in a way that the molar ratios measured in each of the three stages were close or identical to the values from Comparative Experiment A.

Circulation rates were maintained as in Comparative Experiment A and cooling temperatures were slightly adjusted in order to be able to keep the reactor temperatures on a same level as in Comparative Experiment A.

The $SO_3$ concentration of the first, second and third reaction mixture resp. were 14.5%, 13.0% and 12.3% resp. The overall yield measured in the outlet $3^{rd}$ reactor was determined with the above given method to be 99.5%. The extinction at 290 nm (determined as given above) was 0.38.

Comparing Comparative Experiment A with Example 2 shows that the use of oxime as prepared according to the invention results in an increase of the yield to caprolactam and the quality of the obtained caprolactam Comparing Example 2 with Example 3 shows that the use of oxime as prepared according to the invention makes it possible to reduce the quantity of oleum added per quantity of oxime resulting in a lower molar ratio of the reaction mixture in the last stage (and thus a lower amount of ammonium sulfate in the subsequent neutralization) and the yield to caprolactam and the quality of the obtained caproalctam is further improved.

EXAMPLE 4

Comparative Experiment was repeated with the difference that oxime as prepared according to example 1 was used and oleum containing less than 9 wt. % $SO_3$ was used. The oxime feed rates to the three rearrangement stages were left unchanged. To ensure similar oleum to oxime consumption ratios as in Comparative Experiment A the oleum feed rate was eventually set to 10 t/hr as to achieve molar ratios in each of the three stages that are close or identical to the values from Comparative Experiment A.

Circulation rates were maintained as in Comparative Experiment A and cooling temperatures were slightly adjusted in order to be able to keep the reactor temperatures on a same level as in Comparative Experiment A. The $SO_3$ concentration of the first, second and third reaction mixture resp. were 5.0%, 4.4% and 4.2% resp. The overall yield measured in the outlet $3^{rd}$ reactor was determined with the above given method to be 99.3%. The extinction at 290 nm (determined as given above) was 1.06.

Comparing Comparative Experiment A with Example 4 shows that the use of oxime as prepared according to the invention makes it possible to use oleum having a lower $SO_3$ content while the yield to caprolactam and the quality of the obtained caprolactam is further improved.

The invention claimed is:

1. A continuous process for preparing caprolactam in a multi-stage Beckmann rearrangement of cyclohexanone oxime, said process comprising
   a) feeding (i) oleum and (ii) cyclohexanone oxime into a first stage reaction mixture comprising caprolactam, sulfuric acid and $SO_3$,
   b) feeding (iii) a portion of the first stage reaction mixture and (iv) cyclohexanone oxime into a second stage reaction mixture comprising caprolactam, sulfuric acid and $SO_3$, and
   c) withdrawing a portion of the second stage reaction mixture, wherein the process further comprises obtaining the cyclohexanone oxime that is fed to the first and second stage reaction mixtures and is containing less than 1 wt. % water by:
      1) preparing an organic medium comprising cyclohexanone oxime dissolved in an organic solvent
      2) separating, by distillation, cyclohexanone oxime from said organic medium.

2. A process according to claim 1, said process further comprising
   d) feeding (v) a portion of the second stage reaction mixture and (vi) cyclohexanone oxime into a third stage reaction mixture comprising caprolactam, sulfuric acid and $SO_3$, and
   e) withdrawing a portion of the third stage reaction mixture.

3. Process according to claim 2, wherein the cyclohexanone oxime that is fed to the third stage reaction mixtures contains less than 1 wt. % water.

4. Process according to claim 1, wherein the $SO_3$ content of the first and second stage reaction mixtures comprising caprolactam, sulfuric acid and $SO_3$ is at least 6 wt. %.

5. Process according to claim 1, wherein the $SO_3$ content of the first and second stage reaction mixtures comprising caprolactam, sulfuric acid and $SO_3$ is at least 8 wt. %.

6. Process according to claim 1, wherein the $SO_3$ content of the first and second stage reaction mixtures comprising caprolactam, sulfuric acid and $SO_3$ is at least 10 wt. %.

7. Process according to claim 1, wherein the $SO_3$ content of the oleum is between 18 and 35 wt. %.

8. Process according to claim 1, wherein the process comprises:
   a) feeding (i) oleum and (ii) cyclohexanone oxime into the first stage reaction mixture comprising caprolactam, sulfuric acid and $SO_3$,
   b) feeding (iii) a portion of the first stage reaction mixture and (iv) cyclohexanone oxime into a second stage reaction mixture comprising caprolactam, sulfuric acid and $SO_3$, wherein the molar ratio M of the second reaction mixture is between 1.0 and 1.4 and the $SO_3$ content of the second stage reaction mixture is higher than 6 wt. %, and
   c) withdrawing a portion of the second reaction mixture from which caprolactam is recovered.

9. Process according to claim 8, wherein the $SO_3$ content of the second stage reaction mixture is higher than 8 wt. %.

10. Process according to claim 8, wherein the $SO_3$ content of the second stage reaction mixture is higher than 10 wt. %.

11. Process according to claim 1, wherein the process comprising
   a) feeding (i) oleum and (ii) cyclohexanone oxime into the first reaction mixture comprising caprolactam, sulfuric acid and $SO_3$,
   b) feeding (iii) a portion of the first stage reaction mixture and (iv) cyclohexanone oxime into a second stage reaction mixture comprising caprolactam, sulfuric acid and $SO_3$,
   c) withdrawing a portion of the second stage reaction mixture;
   d) feeding (v) a portion of the second stage reaction mixture and (vi) cyclohexanone oxime into a third stage reaction mixture comprising caprolactam, sulfuric acid and $SO_3$, wherein the molar ratio M of the third stage reaction mixture is between 1.0 and 1.4 and the $SO_3$ content of the third stage reaction mixture is higher than 6 wt. %, and e) withdrawing a portion of the third stage reaction mixture from which caprolactam is recovered.

12. Process according to claim 11, wherein the $SO_3$ content of the third stage reaction mixture is higher than 8 wt. %.

13. Process according to claim 11, wherein the $SO_3$ content of the third stage reaction mixture is higher than 10 wt. %.

14. Process according to claim 11, wherein the cyclohexanone oxime that is fed to the first, second and third stage reaction mixtures and contains less than 1 wt. % water is obtained by:

1) preparing an organic medium comprising cyclohexanone oxime dissolved in an organic solvent; and 2) separating, by distillation, cyclohexanone oxime from said organic medium.

15. Process according to claim 14, wherein the cyclohexanone oxime that is fed to the first, second and third stage reaction mixtures contains less than 0.2 wt. % water.

16. Process according to claim 14, wherein the cyclohexanone oxime that is fed to the first, second and third stage reaction mixtures contains less than 0.1 wt. % water.

17. Process according to claim 1, wherein the cyclohexanone oxime that is fed to the first, second and third stage reaction mixtures contains less than 0.2 wt. % water.

18. Process according to claim 1, wherein the cyclohexanone oxime that is fed to the first, second and third stage reaction mixtures contains less than 0.1 wt. % water.

* * * * *